US006835179B2

(12) United States Patent
Husar et al.

(10) Patent No.: US 6,835,179 B2
(45) Date of Patent: Dec. 28, 2004

(54) OPTICAL STIMULATION OF THE HUMAN EYE

(75) Inventors: Peter Husar, Ilmenau (DE); Gunter Henning, Ilmenau (DE); Klaus Schellhorn, Ilmenau (DE); Sebastian Berkes, Ilmenau (DE); Falk Schlegelmilch, Ilmenau (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 10/169,850
(22) PCT Filed: Nov. 21, 2001
(86) PCT No.: PCT/EP01/13475
§ 371 (c)(1),
(2), (4) Date: Nov. 7, 2002
(87) PCT Pub. No.: WO02/41769
PCT Pub. Date: May 30, 2002

(65) Prior Publication Data
US 2003/0125638 A1 Jul. 3, 2003

(51) Int. Cl.[7] .............................................. A61B 13/00
(52) U.S. Cl. ....................................................... 600/558
(58) Field of Search .......................... 600/558; 351/208, 351/210, 211, 222, 224, 226, 221, 237, 246, 243

(56) References Cited

U.S. PATENT DOCUMENTS

| 3,288,546 | A | * | 11/1966 | Gans | ........................... 351/226 |
| 4,685,784 | A | | 8/1987 | Kirchhuebel | |
| 5,220,361 | A | | 6/1993 | Lehmer et al. | |
| 5,323,194 | A | * | 6/1994 | Campbell et al. | ........... 351/226 |
| 5,889,577 | A | | 3/1999 | Kohayakawa | |
| 5,920,375 | A | | 7/1999 | Fahle et al. | |

FOREIGN PATENT DOCUMENTS

DE     4108403 A1 * 10/1991   ........... A61B/3/024

OTHER PUBLICATIONS

International Search Report.
* cited by examiner

Primary Examiner—Mary Beth Jones
Assistant Examiner—Brian Szmal
(74) Attorney, Agent, or Firm—Patterson, Thuente, Skaar & Christensen, P.A.

(57) ABSTRACT

According to the invention, the eye of the subject is lit with light from the non-visible spectrum (infrared light) in such a way that its image, taken with an infrared camera, is of sufficiently high-contrast for an evaluation, so that the actual line of sight can be calculated from the picture based on the characteristics of the eye and that, proceeding from the determined line of sight, the coordinates of the coming optical stimulation can be adjusted in such a way that the intended retinal area is stimulated.

17 Claims, 1 Drawing Sheet

OPTICAL STIMULATION OF THE HUMAN EYE

FIELD OF THE INVENTION

Figure 1:
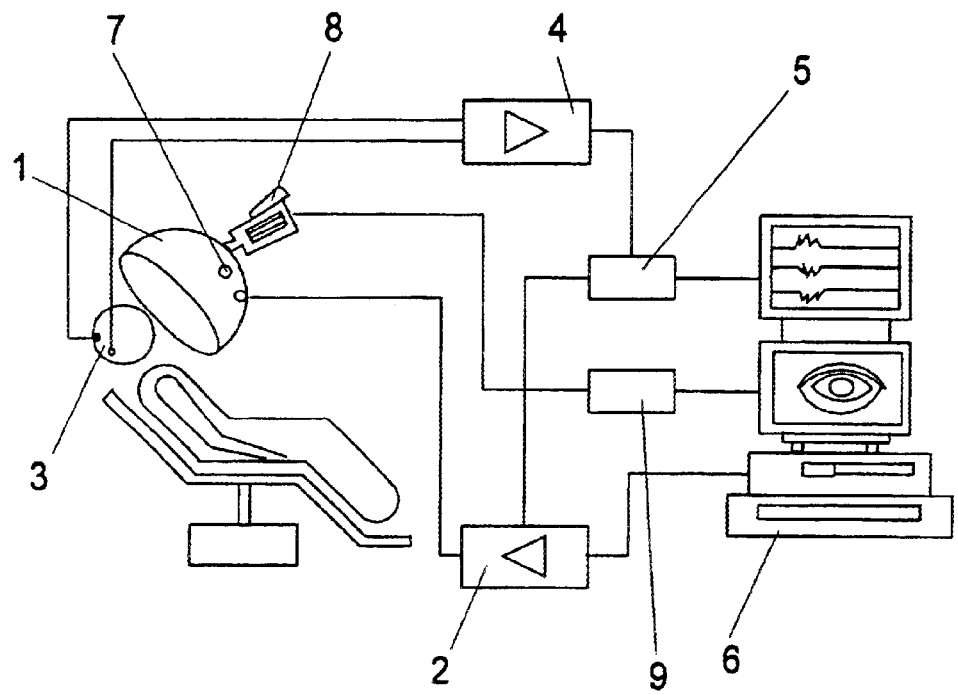

The invention concerns a procedure and an arrangement for the optical stimulation of the human eye by projection of light patterns on the inside of a perimeter hemisphere.

BACKGROUND

Optical stimulation systems that use a spatially fixed coordinate system are known. In the known systems the viewer directs his gaze to a defined visible point in the coordinate system. Under this condition, light stimuli are presented in pre-defined spatial relation to the coordinate system, and the point of fixation. Visible stimuli are projected on a flat or spherical surface, or light sources integrated into the surface may be activated as testing stimuli.

It is known from eye physiology that spontaneous eye movement occurs even when the tested subject deliberately fixedly stares at a fixation point. The angular deviations from the fixation point arising from unintended eye movement can usually be ignored for diagnostic purposes because of their small size.

The current procedures have the disadvantage that testing stimuli are presented in a position relative to the fixation target and not relative to the actual point of fixation. The measured data may therefore be unusable and the examination process is delayed by the need to repeat test stimuli to which responses are deemed unreliable.

The reasons for poor fixation can be of a subjective or objective nature. A typical subjective reason is positive malingering, the simulation of an illness or an impairment by the examined person. Less frequent is negative malingering in which the examined person tries to hide an impairment of the visual field.

Most problems with poor fixation are due to objective reasons: The patients are either not cooperative (small children, psychically ill people, mentally impaired) or have visual field defects already (for example central scotoma), in which case central fixation is not possible. Such patients can therefore not be diagnosed with common methods of examination that are based on the use of a perimeter with fixed coordinates of the optical system.

DESCRIPTION OF THE INVENTION

The invention provides a procedure and arrangement that makes it possible to determine the actual line of sight of the examined person relative to the coordinates of the optical system in such a way that the intended retinal areas can be optically stimulated regardless of the eye movement.

According to the invention, it is intended that during the procedure for the optical stimulation of the human eye by the projection of light pattern on the inside of a perimeter hemisphere that the test stimulus light pattern is projected on the perimeter hemisphere with the help of a light source, an aperture arrangement, a lens arrangement and a light distributor and the position of the test stimulus light pattern on the perimeter hemisphere follows the line of sight of the eye.

In a preferred embodiment of the procedure the light patterns are computer controlled and generated and are adjustable in brightness, color, geometry and time.

In the procedure, according to the invention, the coordinate system of the perimeter constantly follows the actual line of sight of the viewer, so that the intended areas on the retina can always be optically simulated, regardless variations in fixation.

The invention prevents interruption of the perimeter examination due to poor fixation, and is thus an improvement over common methods.

The invention furthermore concerns an arrangement for the stimulation of the human eye by projection of light patterns on the inside of a perimeter hemisphere in which methods are available for the determination of the line of sight of the examined eye during the projection of the light patterns on the perimeter hemisphere.

A preferred method for the determination of the line of sight utilizes an infrared light source and an infrared sensitive camera with digital image processing.

In a further embodiment of the invention the light distributor includes a multi mirror device a D-ILA arrangement, a rotating scanner, a galvano mirror scanner or a combination of these principles.

In the arrangement according to the invention a flat or curved surface is positioned in the field of vision of the viewer. Optical stimuli are provided at pre-defined points with suitable light sources in such a way that they stimulate the intended areas on the retina in their optical projection. The eye movements are captured with a camera and the actual line of sight is determined from the information on the image. Proceeding from the actual line of sight the points of stimulation are then placed on the projection area in such a way that they are positioned relative to the actual point of fixation.

This has the advantage that because of the constant monitoring of the line of sight and the following of the optical system to the change in the line of sight, the desired retinal areas are always stimulated even with movements of the eye. This is an advantage, especially in regards to the reliability and objectivity of the method, even with cooperative patients that are willing to maintain fixation but are not able to do so for physiological reasons. The essential contribution can be seen in the fact that it is still possible to achieve useful diagnostic field results with patients who subjectively or objectively do not maintain fixation. All current methods that utilize a fixed fixation target fail in this area.

SHORT DESCRIPTION OF THE DRAWINGS

Figure 2:
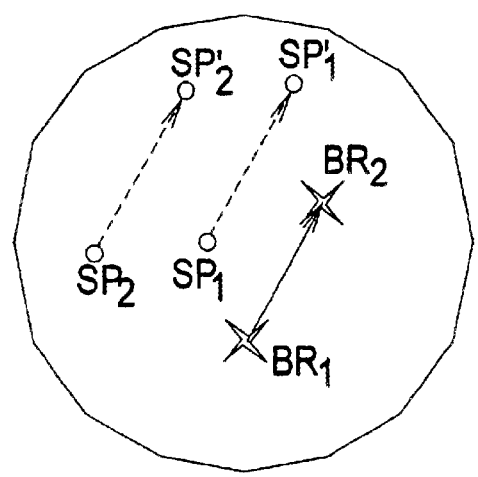

In the following the invention is explained with the help of drawings. Shown are:

FIG. 1 a schematic wiring diagram of the apparatus;

FIG. 2 depicts the principle of the fixation following process

DETAILED DESCRIPTION OF THE DRAWINGS

As shown in FIG. 1 the patient sits in front of a perimeter hemisphere 1, in which a stimulation pattern, generated by the computer 6, is projected from a lighting system 2. The lighted pattern produces responses, typically in the EEG of the examined person. The EEG is captured from the skin of the head of the patient with the help of an EEG electrode system 3, amplified in an amplifier 4 and digitized with an analog-digital converter 5. The EEG is analyzed and evaluated in the digital form in the computer 6.

It is of crucial significance for the success of the examination, that only the desired retinal areas are stimulated at all times. As shown in FIG. 2, the examined person must focus his view on the fixation point BR 1, so that the light stimuli coming from the stimulation points SP1 and SP2 impinge upon the desired area on the retina. If the gaze is not fixated on BR 1 and the examined person changes the line of sight, the stimulation points SP1 and SP2 follow the actual line of sight (fixation point BR2) in order to guarantee the desired stimulation parameter.

For this purpose the eye is illuminated with an infrared light source 7 in such a way that its picture, taken with an infrared camera 8, is of sufficiently high-contrast for an evaluation. Following the digitization in a picture digitizer 9, the picture is evaluated in the computer 6 and the actual line of sight is determined. Afterwards, the fixation point is brought from the initial (BR1) to a new position (BR2) and the stimulation points SP1 and SP2 are spatially moved accordingly (SP1 and SP2). That way it can be guaranteed that the planned retinal areas are always stimulated, even with eye movement.

What is claimed is:

1. A method of presenting visible testing stimuli to a human eye at a perimeter testing surface, the human eye being subject to natural changes in position that result in natural changes in gaze and fixation, the method comprising the steps of:
    (a) first, determining a first point of fixation of the human eye by capturing a first image of the human eye, digitizing the first image and processing the image with a computer to locate the first point of fixation;
    (b) thereafter, presenting a first testing stimulus at a location measured relative to the first point of fixation on a coordinate system having the first point of fixation as its reference point;
    (c) recording a response to the first testing stimulus;
    (d) next, determining a second point of fixation of the human eye by capturing a second image of the human eye, digitizing the second image and processing the image with a computer to locate the second point of fixation;
    (e) presenting a second testing stimulus at a location measured relative to the second point of fixation on the coordinate system now having the second point of fixation as its reference point;
    (f) recording a response to the second testing stimulus and
    (g) repeating steps (d), (e) and (f) for additional points of fixation, testing stimuli and responses to testing stimuli.

2. The method as recited in claim 1, further comprising the step of adjusting the testing stimuli in brightness.

3. The method as recited in claim 1, further comprising the step of adjusting the testing stimuli in color.

4. The method as recited in claim 1, further comprising the step of adjusting the testing stimuli in geometry.

5. The method as recited in claim 1, further comprising the step of adjusting a time between presentations of testing stimuli.

6. The method as recited in claim 1, further comprising the step of illuminating the human eye with infrared light and capturing images with an infrared sensitive camera.

7. The method as recited in claim 1, further comprising the step of presenting the testing stimuli by projection via a multi-mirror-device, a D-ILA arrangement, a rotation scanner, a galvanic mirror scanner or a combination of the foregoing.

8. The method as recited in claim 1, further comprising the step of sensing responses to the testing stimuli via EEG electrodes.

9. A device for optical stimulation of a human eye of a human subject by presentation of stimuli on a perimetry testing surface, comprising:
    a fixation point locator including a video camera, an analog to digital converter and a computer running software that analyzes digitized images of the human eye captured by the video camera to locate a point of fixation at the perimetry testing surface;
    a coordinate system using as its point of reference the located point of fixation,
    a stimulus generator acting in response to the fixation point locator and generating a visual stimulus at the perimetry testing surface at a location relative to the located point of fixation;
    a neurological sensor operably connectable to the human subject to sense a response to the stimulus; and
    a recorder operably connected to the neurological sensor to record the response to the stimulus.

10. The device as claimed in claim 9, in which the stimulus generator comprises a a light source;
    an aperture arrangement;
    a lens arrangement;
    a light distributor; and
    a computer controlling the operation thereof.

11. The device as claimed in claim 10, in which the computer controls the brightness, color, geometry and time sequence of presented stimuli.

12. The device as claimed in claim 9, in which the neurological sensor comprises an EEG operably connected to the human subject.

13. The device as claimed in claim 9, in which the fixation point locator further comprises an infrared illuminator and in which the video camera is adapted to capture infrared light images.

14. The device as claimed in claim 9, in which the stimulus generator comprises a multi-mirror-device, a D-ILA arrangement or as rotation scanner, a galvanic mirror scanner or a combination thereof.

15. The device as claimed in claim 9, in which the stimulus generator comprises a D-ILA arrangement.

16. The device as claimed in claim 9, in which the stimulus generator comprises a rotation scanner.

17. The device as claimed in claim 9, in which the stimulus generator comprises a galvanic mirror scanner.

* * * * *